(12) United States Patent
Pechoux

(10) Patent No.: US 9,028,471 B2
(45) Date of Patent: May 12, 2015

(54) COVER, A TREATMENT DEVICE AND A METHOD OF USE OF SUCH A DEVICE

(75) Inventor: Thierry Pechoux, Paris (FR)

(73) Assignee: Theraclion SAS, Paris (FR)

( * ) Notice: Subject to any disclaimer, the term of this patent is extended or adjusted under 35 U.S.C. 154(b) by 374 days.

(21) Appl. No.: 13/509,895

(22) PCT Filed: Nov. 23, 2010

(86) PCT No.: PCT/EP2010/068034
§ 371 (c)(1),
(2), (4) Date: Jun. 1, 2012

(87) PCT Pub. No.: WO2011/064209
PCT Pub. Date: Jun. 3, 2011

(65) Prior Publication Data
US 2013/0131704 A1    May 23, 2013

(30) Foreign Application Priority Data
Nov. 27, 2009 (EP) .................................. 09177407

(51) Int. Cl.
| | |
|---|---|
| *A61B 18/04* | (2006.01) |
| *A61B 19/02* | (2006.01) |
| *A61B 8/00* | (2006.01) |
| *A61N 7/02* | (2006.01) |
| *A61B 17/00* | (2006.01) |
| *A61B 17/225* | (2006.01) |
| *A61B 18/00* | (2006.01) |

(52) U.S. Cl.
CPC .............. *A61B 19/02* (2013.01); *A61B 8/4422* (2013.01); *A61B 2017/00084* (2013.01); *A61B 2017/2253* (2013.01); *A61B 2018/00023* (2013.01); *A61N 7/02* (2013.01)

(58) Field of Classification Search
CPC ..................... A61B 19/02; A61B 2017/00084; A61B 2017/2253; A61B 2018/00023; A61B 8/4422; A61B 18/1492; A61B 17/2202; A61N 7/02
USPC .......................................................... 606/27
See application file for complete search history.

(56) References Cited

U.S. PATENT DOCUMENTS

| | | | |
|---|---|---|---|
| 4,794,930 A * | 1/1989 | Machida et al. ............... | 600/459 |
| 5,273,027 A | 12/1993 | Sekino et al. | |
| 5,304,115 A * | 4/1994 | Pflueger et al. ................. | 604/22 |
| 5,676,159 A | 10/1997 | Navis | |
| 2005/0113692 A1 | 5/2005 | He et al. | |

FOREIGN PATENT DOCUMENTS

| | | |
|---|---|---|
| DE | 202008013057 | 2/2009 |
| EP | 0146051 | 6/1985 |
| JP | 3122808 | 12/1991 |
| JP | 3122808 | 6/2006 |
| WO | 99/08598 | 2/1999 |
| WO | 2006/129047 | 12/2006 |
| WO | 2008/024515 | 2/2008 |

\* cited by examiner

*Primary Examiner* — George Manuel
(74) *Attorney, Agent, or Firm* — Davis & Bujold, P.L.L.C.; Michael J. Bujold

(57) ABSTRACT

This invention concerns a cover member, especially for a HIFU head, comprising a peripheral outer wall, an open first side configured to partially cover an ultrasound head and a closed second side comprising a flexible membrane adapted for contact with a patient's skin, characterized in that the cover member is removeably attachable to the tip of said ultrasound probe.

26 Claims, 3 Drawing Sheets

COVER, A TREATMENT DEVICE AND A METHOD OF USE OF SUCH A DEVICE

Figure 1:
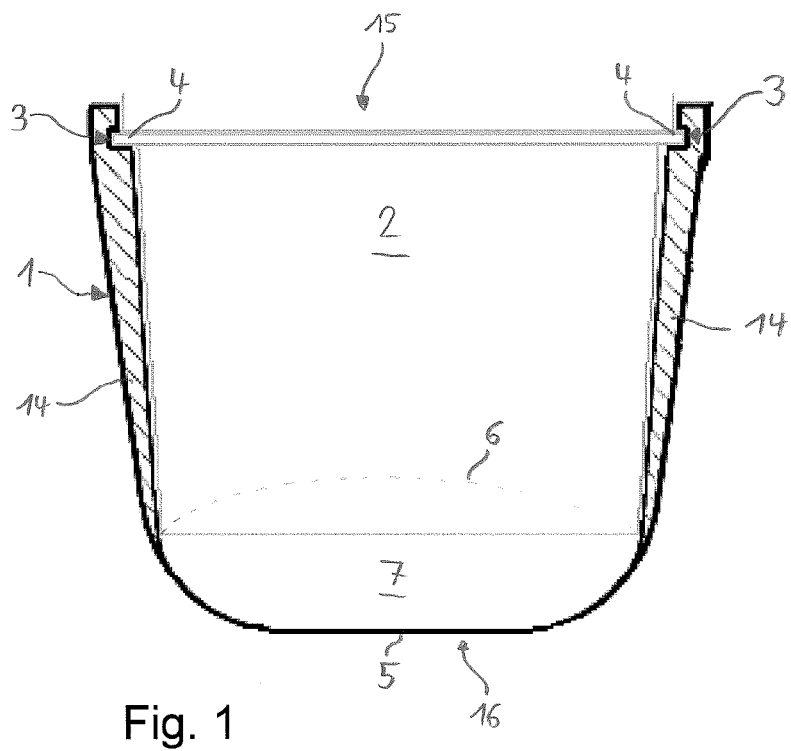

This invention relates to a removable cover member for ultrasound probe heads, especially HIFU (high intensity focused ultrasound) probe heads, to a treatment device and a method of use of such a device according to the preamble of the independent claims.

Treatment of patients with ultrasound waves, particularly high intensity focused ultrasound (HIFU) is well known in the art. It is especially used for treatment of tumours of the thyroid, breast, uterus and prostate. Tumours are thereby destroyed by means of thermal energy. The necessary heat is generated by focussing high intensity ultrasound waves onto a single focal point. As an acoustic wave propagates through the tissue, part of it is absorbed and converted to heat. At the focal point, due to the significant energy deposition, the temperature within the tissue rises to 65° to 85° C., destroying the diseased tissue by coagulation necrosis. One big advantage of treatment with HIFU is that it is a non-invasive treatment method, thereby considerably reducing risks for the patient.

HIFU treatment devices usually comprise a treatment head with a HIFU transducer. The treatment head is placed on the tissue to be treated or on tissue adjacent to the organ to be treated. Such devices are sold e.g. by EDAP TMS under the trademark Ablatherm® or by Theraclion under the name TH-One. In most cases the treatment head comprises a cover membrane defining a space between said membrane and the ultrasound transducer which is filled with coupling liquid. The use of coupling liquid allows ultrasound waves to travel through liquid or similar media without encountering reflective air interfaces between the transducer and the skin of a patient.

The lithotripter Sonolith® Praktis sold by EDAP TMS comprises a removable cover on the ultrasound head to allow mounting of an electrode in the ellipsoidal reflector. The cover is made of a metallic circumferential wall and a flexible membrane on one side. The cover is held on the ultrasound head by means of three metallic clamps. The ellipsoidal reflector covered by the cover member may subsequently be filled with a coupling liquid.

This cover has the disadvantages that it is not easily attachable to the ultrasound head, since all the clamps have to be locked in place separately. Moreover, care must be taken to make the cover leak proof, since different parts of different materials are assembled together.

WO 2009/082874 describes a probe head with such a membrane filled with a gel-like coupling liquid. The probe transducer is cooled by air flow.

WO 2008/081147 relates to a HIFU probe head with a cover membrane defining a chamber filled with acoustic coupling liquid. The chamber is coupled to a closed liquid circuit. By means of pumps the liquid is pumped through the chamber and cooled in a cooling chamber. Therefore the liquid additionally acts as cooling fluid to reduce the temperature of the transducer as well as from the skin of the patient.

In both cases, the membrane needs to be cleaned and/or disinfected together with the probe head.

It is therefore an objective of the present invention to provide for a probe head cover which overcomes the disadvantages of the prior art and in particular to provide a probe head cover, an ultrasound device and a method of use of the ultrasound device with an increased level of hygiene.

The invention concerns a cover member for a HIFU head, comprising a dimensionally stable peripheral outer wall, an open first side configured to partially cover an ultrasound head and a closed second side comprising a flexible membrane adapted for contact with a patient's skin. The cover member is provided with connection means for removable attachment to the tip of said ultrasound probe. The membrane is configured in such a way as to minimize absorption of HIFU ultrasound waves.

The peripheral outer wall is dimensionally stable, it therefore keeps its shape irrespective whether the cover member is mounted on a probe head or not. This dimensional stability can be achieved e.g. by selecting an appropriate thickness and/or material for the wall. Preferably the peripheral outer wall has a shape which is configured as to match the shape of a specific ultrasound head. This facilitates mounting of the cover member on the ultrasound head, since in most cases the cover can just easily be slid onto the probe head. In one specific embodiment, the outer peripheral wall has a frusto-conical shape. Alternatively, the outer peripheral wall may be of a cylindrical, cubic or frustopyramidal shape.

The attachment means are configured to be easily engaged and disengaged with the probe head.

The flexible membrane is configured in such a way as to minimize the absorption or reflection of HIFU waves. When the cover member is assembled onto an ultrasound probe head the flexible membrane will be positioned between the ultrasound transducer and the tissue and/or organ to be treated, therefore reflecting or absorbing some energy from the HIFU ultrasound waves. Having a membrane adapted to minimize this absorption or reflection leads to higher treatment efficiency. Reflection of energy off the membrane is dependent on the thickness and the acoustic impedance of the used material. Minimizing in this sense means that the thickness of the flexible membrane and the acoustic impedance of the material are selected in a way to let a maximum of the ultrasound energy reach the tissue and/or organ to be treated. The flexible membrane absorbs or reflects less than 5% of the ultrasound energy is, more preferably less than 3% and most preferably less than 1%.

Further, the flexible membrane is configured in a way as to provide a high thermal conductivity. This has the beneficial effect that heat from the skin can be easily transferred to a cooling liquid inside a confined space between the cover member and the probe head. Thermal conductivity of the membrane may be influenced by the thickness of the membrane as well as by appropriate choice of material. Preferably, the material of the membrane has a thermal conductivity of more than $0.1\ \mathrm{Wm^{-1}K^{-1}}$, more preferably more than $0.2\ \mathrm{Wm^{-1}K^{-1}}$, and a thickness of less than 100 µm.

The attachment means have to be configured as to withstand a certain dismounting pressure of the coupling and/or cooling liquid which is pumped into a confined space between the cover member and the probe head. Generally the operating pressure will be limited to a few mbar, typically 1 to 5 mbar. Preferably, the attachment means will dismount if the pressure of the coupling and/or cooling liquid exceeds a certain threshold, e.g. 300 mBar. Thus the excess liquid will be able to escape the cover member. This feature has the advantage of protecting the probe head and especially the transducer from over pressure inside the chamber.

The cover member also comprises sealing means such as to render any attachment between the cover and a probe head liquid-tight. This prevents any spillage of coupling and/or cooling liquid.

Each treatment with the ultrasound device may therefore be carried out with a new and clean probe head cover and used cover members may be discarded. Alternatively, the probe head cover may be cleaned and/or sterilised separately from the probe head, e.g. in a standard steam or Ethylene Oxide sterilisator. In comparison to known systems where the membrane can only be cleaned and/or sterilised together with the probe head, e.g. with a sterilization solution, the overall cleanness and sterility is greatly improved.

It is also possible to use cover members made of different materials such that patients suffering from an allergy to one material may be treated using a cover member made of a different material.

Furthermore, various cover members with different shapes allowing for different distances between the patient's skin and the transducer may be used, depending on the minimal depth required for the focal point of the ultrasound. E.g. depending on the treatment to be administered to the patient or the position of the organ and/or tissue to be treated, a cover member allowing for the right distance between the ultrasound head and the tissue and/or organ may be selected.

In a preferred embodiment, the cover member is formed as a single piece. Therefore, the flexible membrane, the outer peripheral wall as well as the attachment means are all on one and the same integral piece.

A cover member made as a single piece has the advantage that the contact area of the cover member with the skin corresponds to the intersection with the skin of the ultrasound beam emitted by the treatment transducer. It is therefore possible to reduce the contact area between tissues of a patient, e.g. the skin, and the cover member to a minimum. Further, configuration of the cover member as a single piece eliminates any assembly steps during production. Hence, it is possible to mould the cover member, thus allowing for a quick and cheap manufacturing.

The cover member is preferably made of at least one elastomeric material. This material preferably comprises a silicone compound. Alternatively, the cover member may also be made of latex. Alternatively, the cover member may also be made of two or more different elastomeric materials. For example, the closed second side, which is adapted for contact to a patient's skin and comprises a flexible membrane, may be made of more elastic material than the outer peripheral wall. Both materials may be moulded in one step.

An elastic peripheral wall offers the advantage that the cover member may be attached to the probe head without the use of a tool or additional fastening means, like screws or spring locks. For example, attachment of the cover member can be achieved by providing a cover member with a slightly smaller circumference than the probe head. When such a cover member is slid over a probe head, the material of the cover member must be deformed to fit over the probe head. When in place, the material will try to relax to its original shape, thus generating a contraction force on the probe head.

The use of elastomers also provides for easy manufacturing of the cover member, since it can be moulded in one piece from a single material. Alternatively, different elastomers may be used to mould the cover member. Elastomeric materials also have the advantage that the material itself will provide for sealing the connection between the cover member and the probe head through the generated contraction force. Moreover, elastomers, such as silicone, are generally biocompatible. Additionally they offer a favourable combination of low acoustic impedance, high extensibility or elongation, mechanical strength and high thermal conductivity.

One embodiment provides for a cover member where the thickness of the elastomeric material varies from the open side towards the closed side to allow for regions with different rigidity and/or elasticity. Preferably the outer peripheral wall is thicker in the area of the open side than in the area of the closed side. Preferably the peripheral outer wall is thicker in the area of the attachment means. In one preferred embodiment, the attachment means are located near the open side of the cover member and the peripheral outer wall has a decreasing thickness from the open side to the closed side.

In another embodiment, the thickness of the elastomeric material of the flexible membrane is about or less than ¼ of the wavelength of the waves emitted by the ultrasound transducer. Preferably the thickness of the flexible membrane is in the range of between 50 μm and 150 μm, most preferably 75 μm for a 3 MHz operation.

When the thickness of the flexible membrane is about ¼ of the wavelength of the used ultrasound, any multiple reflections of the ultrasound waves will be in phase. This will furthermore increase the overall efficiency of the treatment.

Having a thin membrane will also facilitate the transport of heat from the skin to a cooling liquid contained inside the cover member.

The material used for the flexible membrane should have an acoustic impedance which is similar to the acoustic impedance of the coupling and/or cooling liquid to be used and/or the tissue and/or the skin. Preferably the acoustic impedance of the material is between $1.4 \cdot 10^6$ and $1.7 \cdot 10^6$ [Pa·s·m$^{-1}$], preferably about $1.56 \cdot 10^6$ [Pa·s·m$^{-1}$] at room temperature. Using similar acoustic impedances reduces the amount of total reflexions of HIFU waves at the surfaces.

Further, the cover member may be configured in such a way that the flexible membrane may be elastically deformed by at least 25% in relation to its diameter in a direction perpendicular to its surface. The deformation is measured at the centre of the flexible membrane. Deformation of the flexible membrane is preferably carried out by pressure of a coupling and/or cooling liquid.

Deformation of the membrane allows for moving the focal point of the ultrasound transducer along an axis which is perpendicular to the surface of the membrane inside the patient's body. When the membrane is not expanded, the focal point will be at its deepest position. By gradually deforming the membrane in the direction which is opposed to the probe head, therefore moving the probe head away from the tissue and/or organ to be treated, the focal point will also be moved. Preferably, the membrane is expandable to at least 15 mm, more preferably 25 mm in a direction which is perpendicular to its surface for a diameter of 60 mm.

Alternatively, the membrane is elastically deformable by at least 25% of the diameter of the closed second side in a direction perpendicular to its surface compared to the initial configuration of the cover member. For example, if the diameter of the closed side is 60 mm, the membrane will be deformable by at least 15 mm.

A deformation of the membrane will lead to an increase of the volume of the confined space formed between the outer peripheral wall, the membrane and the probe head. Due to the initial configuration of the cover member, the confined space has a certain initial volume. As coupling and/or cooling liquid is pumped into said confined space, this initial volume will be filed by liquid. The filing of said initial volume does not require the use of any pressure. Once said initial volume is filled, the membrane will expand if the pressure of the liquid is increased. Preferably, the membrane is configured in such a way that a pressure increase of 40 mbar leads to an increase of the volume of the confined space of about 10 ml.

The membrane is preferably configured in such a way that its maximal deformation will move the focal point to a minimal treatment depth.

The cover member may comprise at least one inlet opening and at least one outlet opening for a coupling and/or a cooling liquid. A cooling and/or coupling liquid may therefore flow into a space defined between the cover member and the probe head through the at least one inlet opening. Likewise, such a liquid may flow out of said space through the at least one outlet opening. Preferably, the at least one inlet opening and the at least one outlet opening are attached or attachable to a closed liquid circuit. This circuit may comprise at least one pump. By increasing the amount and/or pressure of coupling and/or cooling liquid the distance between the transducer and the skin of the patient may be increased. Likewise, by reducing the amount of liquid, this distance may be decreased. The change of distance can be used to move the focus point of the ultrasound along an axis perpendicular to the flexible membrane of the cover member. Alternatively, the liquid circuit may additionally comprise a cooling and/or heating chamber so as to change the temperature of the coupling and/or cooling liquid.

The inlet opening and the outlet opening may be configured as simple openings on the peripheral outer wall. Alternatively, they may be in the form of protruding tubes. Further, the inlet and outlet openings may comprise attachment means for external tubes, e.g. from a closed liquid circuit.

The coupling and/or cooling liquid is preferably pumped by a pump, which may be a peristaltic pump, through a tube to the inlet opening of the cover member. In a first embodiment, the liquid will then flow between the cover member and the probe head to the confined space. In a second, alternative embodiment, the liquid will flow through openings on the probe head into the probe head, meaning in the space between the transducer(s) and the inner wall of the probe head before reaching the confined space. The flexible membrane can be expanded by increasing the pressure and/or the amount of liquid. The liquid can flow out of the probe head/cover member assembly by means of the outlet opening. The outlet opening may be directly connected to a reservoir or a cooling chamber by tubes. Alternatively, a second pump and/or a valve may be provided between the outlet opening and the reservoir and/or cooling chamber. Use of a cooling chamber allows for regulating the temperature of the liquid such as to apply cooling on the transducer and/or the patient's skin.

The attachment means may be arranged on the inside of said peripheral outer wall engaging or being engageable to attachment means on the outside of said ultrasound head.

Such a configuration allows for an easy and reversible attachment of the cover member onto the ultrasound probe head. This can easily be done by partially sliding the cover member over the tip of the probe head and engaging the attachment means with one another, therefore securely locking the cover member on the probe head.

One embodiment of the invention provides for attachment means on the inside of said peripheral wall which is at least one circumferential groove. The attachment means on the ultrasound head is at least one circumferential ridge. The ridge is configured in such a way as to be engageable into said groove.

This embodiment of the attachment means has the advantage that the cover member can easily be attached and removed from the probe head, while still providing a firm connection. Further it provides a tight attachment between the cover member and the probe head, therefore preventing spillage of coupling and/or cooling liquid. Moreover, such a configuration is able to absorb force generated by expansion of the flexible membrane. When cooling and/or coupling liquid is pumped into the confined space, the peripheral wall of the cover member will slightly expand the radial direction in the area surrounding that confined space. This expansion leads to a slight compression force on the side of the cover member around the probe head. Thus the ridge is more tightly pressed into the groove.

Further, in the case that too much coupling and/or cooling liquid is pumped into the space between the cover member and the probe head, the cover member will be pressed away from the probe head due to the increased pressure. This will force the ridge out of the groove, thus causing the disassembly of the cover member from the probe head. This reduces the risk of damage to the transducer. Preferably, the cover member is configured in such a way that the attachment means will disassemble at pressures of the liquid of more than 100 or 300 mBar.

Alternatively, the ridge and the groove may be discontinuous instead of integrally circumferential. In another alternative embodiment, the fastening means on the inside of the peripheral outer wall of the cover member may comprise multiple ridges alternating with multiple grooves, either one above the other or one behind the other arranged on a circumferential circle.

Yet another embodiment of the present invention provides for the cover member additionally comprising at least one ridge on the inside of said peripheral outer wall.

The at least one additional ridge provides for a liquid tight seal when the cover member is mounted on an ultrasound probe head, thereby preventing any coupling and/or cooling liquid to flow out of the confined space. This at least one ridge is configured in such a way that its inward surface is lightly pressed against the probe head when mounted. For better tightness, the cover head may comprise more than one such ridges, preferably 2, 3, or 5.

The ridges may also be arranged in a way to form a channel in between two of the ridges. These ridges may be configured in such a way as to guide the liquid from the inlet to an opening on the surface of the probe head as well as from a second opening of the probe head to the outlet. This allows for optimized flow of liquid independent of the radial alignment of the cover member on the probe head.

In a further alternative embodiment, the cover member further comprises at least one pulling means on the outside of said peripheral outer wall.

Such a pulling mean helps mounting and dismounting the cover member from the probe head. By pulling, a part of the cover member will bulge out and the ridge will loose its connection with the groove. The cover member may then be dismounted by pulling it downwards.

In a preferred embodiment, the pulling mean is in the form of at least one pulling tab.

In an alternative embodiment, the cover member comprises markings on its outer side to help a user to correctly align the cover member on the probe head. This facilitates the subsequent connection with the tubes carrying the cooling and/or coupling liquid.

Generally, the cover member may be of any suitable shape. For practical reasons it is preferred that the cover member has a cup-like shape. The flexible membrane thereby defines the base of the cup. The flexible membrane is preferably of circular shape, but may also configured to any suitable shape, such as rectangular or polygonal. The peripheral outer wall can also be adapted to different suitable shapes to fit the probe head, but will preferably also define a circular shape, such as frustoconical.

The ultrasound treatment device comprises at least:
an ultrasound probe head;
an ultrasound transducer, preferably a HIFU transducer located in said ultrasound probe head;
a removable cover member being attachable to the ultrasound probe head; and
attachment means for attaching the cover member on the probe head.

The cover member is removably attached or attachable to said ultrasound probe head thereby creating a confined space between said peripheral outer wall of said cover member and the ultrasound probe head.

Having a system with a removable cover member increases the hygiene of the treatment and shortens the time between two treatments, since instead of having to clean and/or disinfect the membrane attached to the probe head, a new or freshly cleaned and/or disinfected cover member may be mounted.

Attachment means are provided to reversibly attach the cover member on the probe head. Such attachment means may be for example screw threads, clamps, pins and the like. Preferably, the attachment means comprise at least one ridge and at least one groove which are configured to engage into each other. The groove may, for example, be arranged on the inside of the peripheral outer wall of the cover member while the ridge may be arranged on the outside of the probe head.

Moreover, if the patient to be treated suffers from allergy to the material of the cover member, it may quickly be replaced by a cover member made of a different material.

It is also possible to mount a cover member adapted to a specific treatment depth and/or adapted to a specific coupling and/or cooling liquid.

In an alternative embodiment, the ultrasound treatment device further comprises a cooling and/or coupling liquid circuit comprising at least one cooling chamber and at least one pump. The pump is preferably a peristaltic pump. The cooling and/or coupling liquid is pumped through said confined space.

In one embodiment of the present invention the liquid flows between the outer peripheral wall of the cover member and the probe head into the confined space. In another embodiment, openings are provided on the probe head, which allow the liquid to flow between the inside of the probe head wall and the ultrasound transducer.

This embodiment allows for adjustment of the temperature of the coupling and/or cooling liquid. The ultrasound transducer as well as the skin of the patient will be heated by the ultrasound pulses. To allow for proper functioning of the transducer and to avoid burning the skin of the patient, it is advantageous to cool down the coupling liquid or to use a cooling liquid. The temperature may be adjusted by the temperature of the at least one cooling chamber as well as by the flow rate of the liquid, which may be influence through the pump rate.

The liquid circuit preferably further comprises a replaceable pouch containing coupling and/or cooling liquid. Thus the liquid can be replaced quickly and easily by using a new pouch of fresh liquid. The cooling chamber may be in the form of a simple ice water bath. Alternatively, the cooling chamber may comprise cooling plates, such as Peltier elements. Additional sensor means are preferably present in the liquid circuit, such as pressure or temperature measuring sensors. In a special embodiment, the liquid circuit comprises two pumps, one connected to the inlet opening and one connected to the outlet opening of the cover member. This configuration allows for adjustment of the rate of inflow and outflow of the liquid and thus also enables control of the liquid pressure. Such a liquid circuit is e.g. described in the WO 2008/081147, which is hereby incorporated by reference.

Preferably control means are further comprised in an embodiment with a closed liquid circuit. The control means e.g. allow to control the pump rate, the pressure of the liquid, the flow rate and/or the temperature of the liquid. Suitable control means may e.g. be a computer.

Another objective of the present invention is to provide for a method of using an ultrasound device.

The method comprises the steps of:

mounting a cover member comprising a peripheral outer wall, an open first side and a closed second side comprising a flexible membrane configured in such a way as to minimize absorption of HIFU ultrasound waves over the tip of an ultrasound probe head;

engaging attachment means of said cover member with attachment means of said ultrasound probe head; and filling a confined space between the flexible membrane of the cover member and the ultrasound transducer with a coupling and/or a cooling liquid.

This method allows for the use of an ultrasound treatment device with a removable and preferably disposable cover member, thus increasing the overall hygiene of the treatment and also shortening the time between two treatments.

A further embodiment of the method provides for an additional step of connecting tubes to an inlet opening and an outlet opening of the cover member prior to step (c).

Thus, the confined space may be connected to a liquid circuit, providing e.g. for cooling of the liquid. Alternatively, the flexible membrane of the cover member may be elastically deformed by increasing the pressure of the liquid.

Figure 2A:
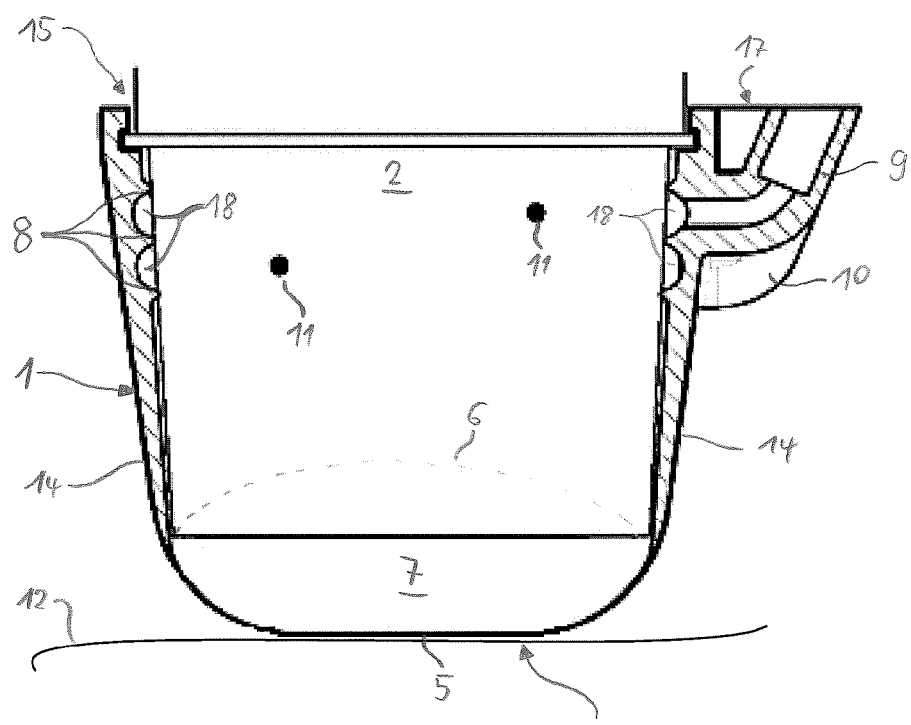
Figure 2B:
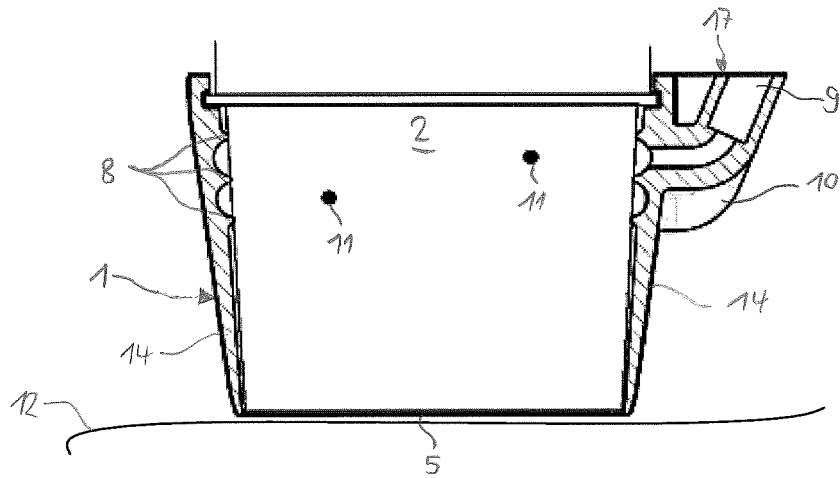
Figure 3:
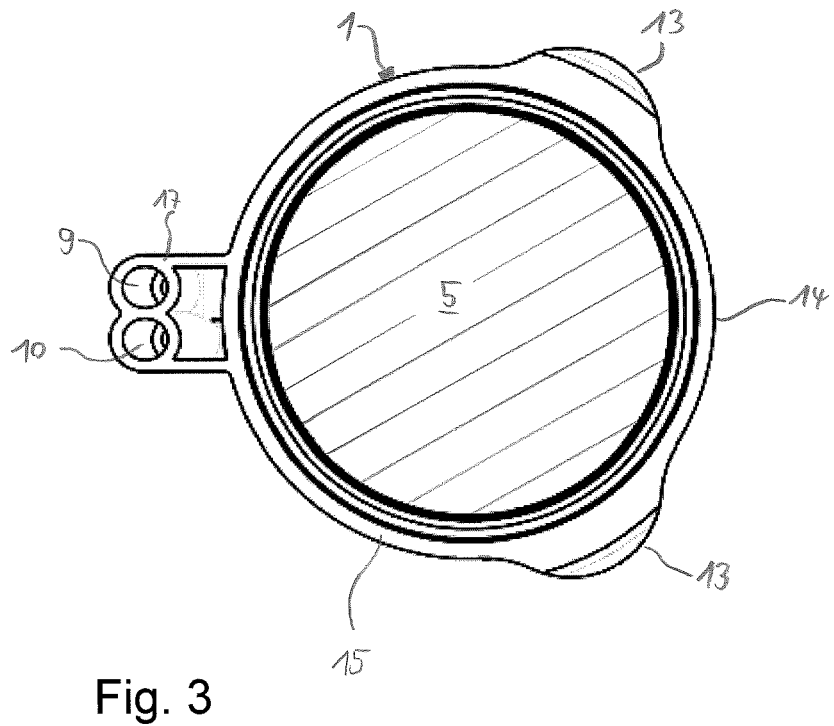
Figure 4:
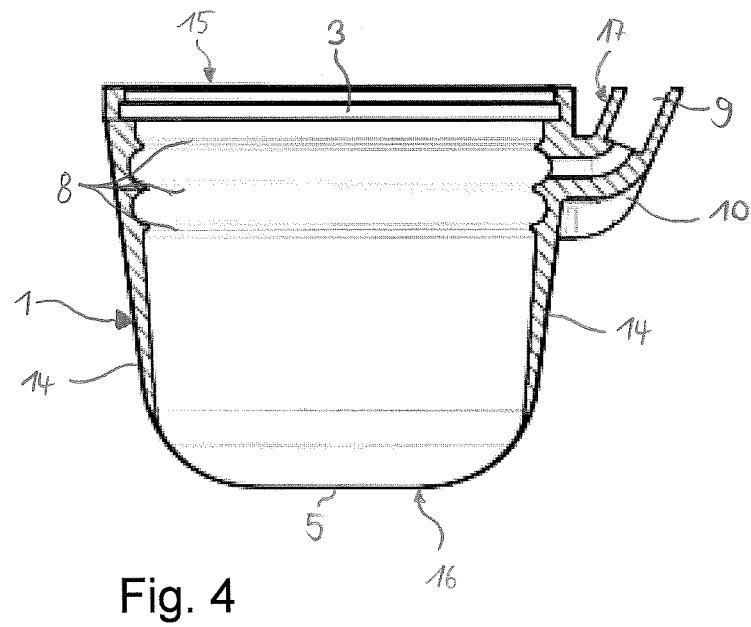

Further details and benefits of the present invention will be apparent from the following figures and examples:

FIG. 1 an exemplary embodiment of the cover member mounted on an ultrasound probe head FIG. 2a an alternative embodiment of the cover member with inlet and outlet for cooling and/or coupling liquid mounted on an ultrasound probe with an expanded membrane FIG. 2b the cover member from FIG. 2a in an unexpanded state FIG. 3 top view of another alternative embodiment of the cover member with pulling tabs FIG. 4 cover member as shown on FIG. 2 dismounted from the probe head FIG. 1 shows an exemplary embodiment of a cover member 1 according to the invention. The cover member comprises a peripheral outer wall 14, a flexible membrane 5 and an open side configured to be slid over a probe head 2. The probe head 2 comprises an ultrasound transducer 6. The area between the probe head 2 and the flexible membrane 5 defines a confined space 7, which may be filled with a coupling and/or cooling liquid. Cover member 1 is attachable to probe head 2 by attachment means of the cover member 1 and attachment means of the probe head 2. This figure shows one exemplary embodiment of the attachment means. A circumferential groove 3 is provided as attachment means on the inside of the cover member 1. The groove 3 is configured to fit over a ridge 4 formed on probe head 2. In this embodiment, groove 3 is arranged near the open side 15 of cover member 1 and extends circumferentially around the entire inside of peripheral outer wall 14. Alternatively, groove 3 and ridge 4 may be intermittent.

Cover member 1 is made a single piece of an elastomeric material and is thus flexible enough to be slightly spread apart so that the part of peripheral outer wall 14 which is above the groove can be slid over the ridge. Once the ridge and the groove are aligned, the spread outer wall 14 will relax and the ridge will engage the groove. Thus a stable connection between cover member 1 and probe head 2 can be established. By again spreading apart outer wall 14 and pulling cover member 1 away from probe head 2 it is possible to disassemble cover member 1 from probe head 2.

In one preferred embodiment cover member 1 is made of an elastomeric material comprising a silicone compound, most preferably MED-4050 obtainable from NuSil Silicone Technology of Carpentera, Fla.

In another embodiment, open side 15 of cover member 1 has a circular shape with a diameter of between 10 mm and 200 mm, preferably 66 mm. The closed side 16 comprising the flexible membrane 5 also preferably has a circular shape with a diameter of between 10 mm and 200 mm, preferably 60 mm. The flexible membrane 5 may comprise the entire area of the closed side. Alternatively, the flexible membrane 5 may have a slightly smaller diameter than the closed side, preferably about between 70% and 99% of the diameter of the closed side, most preferably about 90%.

Yet in another embodiment, the peripheral outer wall 14 has a height of between 30 mm and 100 mm, preferably between 45 mm and 50 mm between the open side 15 and the closed side 16. The thickness of the peripheral outer wall 14 is constant over the entire height. Alternatively, the peripheral outer wall 14 may have a varying thickness. In one exemplary embodiment, the thickness of the peripheral outer wall 14 decreases from the open side 15 to the close side 16. For example the peripheral outer wall 14 may have a thickness of 4.6 mm in the area of the open side 15 and decrease to a thickness of 1.5 mm in the area of the closed side 16.

In one embodiment, cover member 1 is configured in such a way that, when it is assembled to probe head 2, the membrane 5 is at a distance of 15 mm in its initial state from probe head 2. Alternatively, depending on the treatment method, the organ and/or tissue to be treated, the cover member 1 may be configured to provide for other distances between the membrane 5 and the probe head 2, e.g. 5 mm, 8 mm, 13 mm and others.

FIG. 2a shows another embodiment of the present invention. In this embodiment probe head 1 additionally comprises inlet opening 9 and outlet opening 10. A coupling and/or cooling liquid may be pumped into confined space 7 through inlet opening 9. Outlet opening 10 is used to evacuate air while filling confined space 7 and may also serve to remove or pump out the coupling and/or cooling fluid. In a preferred embodiment, inlet opening 9 and outlet opening 10 are connected via tubes to a closed liquid circle comprising at least one pump and at least one cooling and/or heating chamber. When such a closed liquid circle is used, it is possible to control the amount and/or the pressure of cooling and/or coupling liquid in confined space 7 (and thus also expansion of flexible membrane 5) as well as the temperature of said liquid.

Cover member 2 further comprises three circumferential ridges 8 on the inside of peripheral wall 14. Ridges 8 are configured such that their inward surfaces protrude from the internal surface of peripheral outer wall 14 in such a way that these surfaces will be slightly pressed against probe head 2 when cover member 1 is assembled to it. In one embodiment, these ridges 8 serve as liquid tight seals to prevent the coupling and/or cooling liquid to be spilled out of the assembly of cover member 1 with probe head 2. However, in the embodiment as shown, the ridges 8 serve to form channels 18 on the inner side of peripheral wall 14. These channels 18 can be configured in such a way as to guide the flow of liquid to openings 11 on the outside of probe head 2. The liquid will then fill the space between the inside of the peripheral wall of the probe head 2 and the ultrasound transducer 6 as well as confined space 7. Openings 11 may be arranged in such a way as to optimize the flow of liquid. Flexible membrane 5 is placed on the skin 12 of a patient to be treated.

In a preferred embodiment, inlet opening 9 and outlet opening 10 are extended outwardly by means of tubing bulge 17. This allows for easier connection of inlet opening 9 and outlet opening 10 with external tubes, e.g. from a liquid circuit.

The at least one inlet opening 9 and the at least one outlet opening 10 have a diameter of between 3 mm and 5 mm. In a preferred embodiment, inlet opening 9 and outlet opening 10 have a diameter of 3.2 mm. In an alternative embodiment, the at least one inlet opening 9 and the at least one outlet opening 10 have connection means to allow a liquid circuit to be connected. This connection means are preferably in the form of an enlarged diameter to allow for insertion of tubes.

FIG. 2b shows the same embodiment of cover member 1 as shown on FIG. 2a, with the difference that the pressure of the cooling and/or coupling liquid is such that flexible membrane 5 is in its initial state. Thereby confined space 7 is at its minimal volume. Such a configuration may be used when the focal point of ultrasound transducer 6 has to be moved to a maximal treatment depth.

On FIG. 3 a top view of an alternative embodiment is depicted. In this embodiment, two pulling tabs 13 are arranged on the outer side of peripheral wall 14. Cover member 1 has a circular shape to be adapted on a circular probe head. The position of both pulling tabs 13 is about 120° from the centre of tubing bulge 17.

FIG. 4 shows a cross section of the embodiment of the cover member 1 as shown on FIG. 2 dismounted from the probe head. As can be seen on this figure, both the groove serving as attachment means on the inside of the cover member 3 as well as ridges 8 are circumferential and entirely stretch around the inside of peripheral outer wall 14. The embodiment as shown has a circular configuration and its top view matches the one as seen on FIG. 3.

The invention claimed is:

1. Cover member for a HIFU head, comprising a peripheral outer wall being dimensionally stable, an open first side configured to partially cover an ultrasound head and a closed second side comprising a flexible membrane for contact with a patient's skin, said cover member provided with connection means for removable attachment to the tip of said ultrasound probe, wherein said membrane is configured in such a way as to minimize absorption of HIFU ultrasound waves, wherein he membrane absorbs or reflects less than 5% of he ultrasound HIFU waves.

2. Cover member according to claim 1, wherein said cover member comprising said connection means and said flexible membrane is formed as a single piece.

3. Cover member according to claim 1, wherein the membrane is further configured in such a way as to provide a high thermal conductivity.

4. The cover member according to claim 1, wherein it is made of at least one elastomeric material.

5. A cover member according to claim 4, wherein the elastomeric material comprises a silicone compound.

6. The cover member according to claim 1, wherein the thick-ness of the peripheral outer wall varies from said first open side to said closed second side to allow for regions with different rigidity and/or elasticity.

7. The cover member according to claim 1, wherein the thickness of the flexible membrane is about ¼ of the wavelength of the HIFU waves.

8. A cover member according to claim 7, wherein the thickness of the flexible membrane is in the range of between 50 μm and 150 μm.

9. The cover member according to claim 1, wherein the flexible membrane has an acoustic impedance of between $1.4 \cdot 10^6$ and $1.7 \cdot 10^6$ Pa·s·m$^{-1}$.

10. A cover member according to claim 9, wherein the flexible membrane has an acoustic impedance about $1.56 \cdot 10^6$ Pa·s·m$^{-1}$ at room temperature.

11. The cover member according to claim 1, wherein said cover member is configured in such a way that the flexible membrane is elastically deformable by at least 25% of the diameter of the closed second side in a direction perpendicular to its surface compared to its initial configuration.

12. The cover member according to claim 1, wherein said cover member is elastically deformable by at least 15 mm in a direction perpendicular to its surface compared to its initial configuration.

13. The cover member according to claim 1, further comprising at least one inlet opening and at least one outlet opening for coupling and/or cooling liquid.

14. The cover member according to claim 13, wherein said inlet opening and said outlet opening further comprise attachment means for external tubes.

15. The cover member according to claim 1, wherein said attachment means are arranged on the inside of said peripheral outer wall engaging or being engageable to attachment means on the outside of said ultrasound head.

16. The cover member according to claim 15, wherein said attachment means is at least one circumferential groove being engageable with at least one circumferential ridge arranged on the outside of said probe head.

17. The cover member according to claim 1, wherein the cover member additionally comprises at least one ridge on the inside of said peripheral outer wall.

18. The cover member according to claim 1, wherein the cover member further comprises at least one pulling means on the outside of said peripheral outer wall.

19. A cover member according to claim 18 wherein the pulling means is at least one pulling tab.

20. Ultrasound treatment device at least comprising:
   an ultrasound probe head,
   a HIFU transducer located in said ultrasound probe head, and
   a cover member as claimed in claim 1,
   wherein said cover member is removably attached or attachable to said ultrasound probe head thereby creating a confined space between said peripheral outer wall and said flexible membrane of said cover member and the ultrasound probe head.

21. The treatment device according to claim 20, wherein said treatment device further comprises a cooling and/or coupling liquid circuit comprising at least one cooling chamber and at least one pump, whereby said cooling and/or coupling liquid is pumped through said confined space.

22. The treatment device as characterized in claim 21, wherein said liquid circuit further comprises a replaceable pouch with sterile cooling and/or coupling liquid.

23. A treatment device according to claim 21, wherein the pump is a peristaltic pump.

24. Method of operation of an ultrasound treatment device comprising the steps of:
   (a) first mounting a cover member according to claim 1 on the tip of a probe head;
   (b) then engaging attachment means of the cover member with attachment means of the probe head thereby creating a confined space between said peripheral outer wall and said flexible membrane of said cover member and the ultrasound probe head; and
   (c) then filling the confined space with a coupling and/or cooling liquid.

25. The method according to claim 24, further comprising the step of connecting tubes to said inlet and said outlet prior to step (c).

26. Set of at least two cover members with different shapes for a HIFU head according to claim 1, wherein said different shapes are configured in such a way as to provide for different minimal distances between the treatment transducer and the skin of a patient when the membrane is in its initial state.

* * * * *